United States Patent
Parekh et al.

(10) Patent No.: US 11,058,468 B2
(45) Date of Patent: Jul. 13, 2021

(54) BONE FIXATION DEVICE AND METHOD OF USE

(71) Applicant: Additive Orthopaedics, LLC, Little Silver, NJ (US)

(72) Inventors: Selene G. Parekh, Cary, NC (US); Gregory J. Kowalczyk, Little Silver, NJ (US); Brian R. McLaughlin, Yarmouth, ME (US)

(73) Assignee: Additive Orthopaedics, LLC, Little Silver, NJ (US)

( * ) Notice: Subject to any disclaimer, the term of this patent is extended or adjusted under 35 U.S.C. 154(b) by 88 days.

(21) Appl. No.: 15/665,097

(22) Filed: Jul. 31, 2017

(65) Prior Publication Data

US 2018/0028242 A1    Feb. 1, 2018

Related U.S. Application Data

(60) Provisional application No. 62/368,370, filed on Jul. 29, 2016.

(51) Int. Cl.
*A61B 17/80* (2006.01)
*A61B 17/72* (2006.01)
(Continued)

(52) U.S. Cl.
CPC ...... *A61B 17/8061* (2013.01); *A61B 17/7291* (2013.01); *A61B 17/809* (2013.01);
(Continued)

(58) Field of Classification Search
CPC .............. A61B 17/7291; A61B 17/809; A61B 17/8095; A61B 17/8061
See application file for complete search history.

(56) References Cited

U.S. PATENT DOCUMENTS

| 5,211,664 A | 5/1993 | Tepic et al. |
| 5,360,448 A | 11/1994 | Thramann |

(Continued)

FOREIGN PATENT DOCUMENTS

| FR | 2827157 A1 | 1/2003 |
| WO | 2012/109748 A1 | 8/2012 |

(Continued)

OTHER PUBLICATIONS

International Search Report and Written Opinion of the International Searching Authority of PCT/US2017/036004, dated Sep. 13, 2017.

(Continued)

*Primary Examiner* — Olivia C Chang
(74) *Attorney, Agent, or Firm* — Collard & Roe, P.C.

(57) ABSTRACT

There is an implant, comprising a plate portion at a first end, and a stem portion at a second end extending away from an end of the plate portion. In one embodiment, the plate portion comprises a first lobe with a first screw hole; and a second lobe with a second screw hole, wherein the first lobe is adjacent to the second lobe. There is also method of inserting an implant, comprising preparing a patient's bones, performing an osteotomy on the patient's bones to form a first bone segment and a second bone segment, aligning the first bone segment and the second bone segment and inserting an implant into an intramedullary canal in the second bone segment.

13 Claims, 19 Drawing Sheets

(51) Int. Cl.
*A61B 17/00* (2006.01)
*A61B 17/56* (2006.01)

(52) U.S. Cl.
CPC ...... *A61B 17/8057* (2013.01); *A61B 17/8095* (2013.01); *A61B 2017/00831* (2013.01); *A61B 2017/565* (2013.01)

(56) References Cited

U.S. PATENT DOCUMENTS

| | | | |
|---|---|---|---|
| 5,650,108 A | 7/1997 | Nies et al. | |
| 5,856,367 A | 1/1999 | Barrows et al. | |
| 5,869,080 A | 2/1999 | McGregor et al. | |
| 5,876,452 A | 3/1999 | Athanasiou et al. | |
| 6,149,688 A | 11/2000 | Brosnahan et al. | |
| 6,206,924 B1 | 3/2001 | Timm | |
| 6,228,111 B1 | 5/2001 | Toermaelae et al. | |
| 6,235,225 B1 | 5/2001 | Okada et al. | |
| 6,432,107 B1 | 8/2002 | Ferree | |
| 6,436,426 B1 | 8/2002 | Liao et al. | |
| 6,511,511 B1 | 1/2003 | Slivka et al. | |
| 6,527,810 B2 | 3/2003 | Johnson et al. | |
| 6,530,956 B1 | 3/2003 | Mansmann | |
| 6,626,945 B2 | 9/2003 | Simon et al. | |
| 6,840,960 B2 | 1/2005 | Bubb | |
| 7,235,079 B2 | 6/2007 | Jensen et al. | |
| 7,241,313 B2 | 7/2007 | Unwin et al. | |
| 7,351,280 B2 | 4/2008 | Khairoun et al. | |
| 7,578,851 B2 | 8/2009 | Dong et al. | |
| 7,879,109 B2 | 2/2011 | Borden et al. | |
| 7,892,265 B2 | 2/2011 | Perez-Cruet et al. | |
| 7,910,690 B2 | 3/2011 | Ringeisen et al. | |
| 7,943,677 B2 | 5/2011 | Papangelou et al. | |
| 8,119,152 B2 | 2/2012 | Shikinami | |
| 8,292,967 B2 | 10/2012 | Brown et al. | |
| 8,337,873 B2 | 12/2012 | Mao | |
| 8,383,024 B2 | 2/2013 | Morrissette et al. | |
| 8,389,588 B2 | 3/2013 | Ringeisen et al. | |
| 8,445,554 B2 | 5/2013 | Ringeisen et al. | |
| 8,475,505 B2 | 7/2013 | Nebosky et al. | |
| 8,500,843 B2 | 8/2013 | Grohowski | |
| 8,529,625 B2 | 9/2013 | Farrar et al. | |
| 8,535,357 B2 | 9/2013 | Stone et al. | |
| 8,657,827 B2 | 2/2014 | Fitz et al. | |
| 8,700,198 B2 | 4/2014 | Conway et al. | |
| 8,715,366 B2 | 5/2014 | Borden | |
| 2003/0009225 A1 | 1/2003 | Khandkar et al. | |
| 2003/0199875 A1 | 10/2003 | Mingozzi et al. | |
| 2004/0082999 A1 | 4/2004 | Mathys, Jr. et al. | |
| 2004/0243237 A1 | 12/2004 | Unwin et al. | |
| 2004/0258732 A1 | 12/2004 | Shikinami | |
| 2005/0187555 A1 | 8/2005 | Biedermann et al. | |
| 2006/0111715 A1 | 5/2006 | Jackson | |
| 2006/0241763 A1 | 10/2006 | Paul et al. | |
| 2006/0276788 A1 | 12/2006 | Berry et al. | |
| 2007/0156240 A1 | 7/2007 | Tsuang et al. | |
| 2007/0161985 A1 | 7/2007 | Demakas et al. | |
| 2007/0203584 A1 | 8/2007 | Bandyopadhyay et al. | |
| 2008/0269893 A1 | 10/2008 | Bhatnagar et al. | |
| 2009/0187249 A1 | 7/2009 | Osman | |
| 2009/0240324 A1 | 9/2009 | Smith | |
| 2010/0042214 A1* | 2/2010 | Nebosky | A61B 17/56 623/16.11 |
| 2010/0094420 A1 | 4/2010 | Growhowski, Jr. | |
| 2010/0249851 A1 | 9/2010 | Kay et al. | |
| 2010/0262245 A1 | 10/2010 | Alfaro et al. | |
| 2011/0004307 A1 | 1/2011 | Ahn et al. | |
| 2011/0071635 A1 | 3/2011 | Zhang et al. | |
| 2011/0172775 A1 | 7/2011 | Flickinger et al. | |
| 2011/0218626 A1* | 9/2011 | Krinke | A61F 2/28 623/16.11 |
| 2011/0301709 A1 | 12/2011 | Kraus et al. | |
| 2012/0089197 A1 | 4/2012 | Anderson | |
| 2012/0271361 A1 | 10/2012 | Zhou et al. | |
| 2012/0271362 A1 | 10/2012 | Martineau et al. | |
| 2012/0330420 A1 | 12/2012 | Brodke et al. | |
| 2013/0022943 A1 | 1/2013 | Collins et al. | |
| 2013/0066435 A1 | 3/2013 | Averous et al. | |
| 2013/0090733 A1 | 4/2013 | Kraft et al. | |
| 2013/0116793 A1 | 5/2013 | Kloss | |
| 2013/0150965 A1 | 6/2013 | Taylor et al. | |
| 2013/0178900 A1 | 7/2013 | Fallin et al. | |
| 2013/0211533 A1 | 8/2013 | Fonte et al. | |
| 2014/0039565 A1 | 2/2014 | Martineau et al. | |
| 2014/0107785 A1 | 4/2014 | Geisler et al. | |
| 2014/0180432 A1 | 6/2014 | Conway et al. | |
| 2014/0188237 A1 | 7/2014 | McCormick et al. | |
| 2014/0277554 A1 | 9/2014 | Roman et al. | |
| 2015/0032220 A1 | 1/2015 | Tyber et al. | |
| 2015/0045903 A1 | 2/2015 | Neal | |
| 2015/0088201 A1 | 3/2015 | Massoudi | |
| 2015/0100126 A1 | 4/2015 | Melkent et al. | |
| 2015/0100129 A1 | 4/2015 | Waugh et al. | |
| 2015/0142066 A1 | 5/2015 | Shemwell et al. | |
| 2015/0150607 A1 | 6/2015 | Chen et al. | |
| 2015/0250513 A1 | 9/2015 | De Lavigne Sainte Suzanne | |
| 2016/0089138 A1 | 3/2016 | Early et al. | |
| 2017/0239059 A1 | 8/2017 | Boublil et al. | |

FOREIGN PATENT DOCUMENTS

| | | |
|---|---|---|
| WO | 2014/068259 A1 | 5/2014 |
| WO | 2016/027025 A2 | 2/2016 |
| WO | 2016/177790 A1 | 11/2016 |

OTHER PUBLICATIONS

International Search Report and Written Opinion of the International Searching Authority of PCT/US2017/030701, dated Aug. 3, 2017.

International Search Report and Written Opinion of the International Searching Authority of PCT/US2017/044740, dated Nov. 17, 2017.

International Search Report and Written Opinion of the International Searching Authority of PCT/US2015/052121, dated Nov. 19, 2015.

International Preliminary Report on Patentability and Written Opinion of the International Searching Authority of PCT/US2017/044740 dated Jan. 29, 2019.

* cited by examiner

BONE FIXATION DEVICE AND METHOD OF USE

CROSS SECTION TO RELATED APPLICATIONS

This application is a non-provisional application that hereby claims priority from U.S. Provisional application Ser. No. 62/368,370 filed on Jul. 29, 2016 the disclosure of which is hereby incorporated herein by reference.

FIELD OF THE INVENTION

The present invention relates generally to general surgery, and more particularly orthopaedic and podiatric surgery. More specifically, but not exclusively, the present invention concerns implants used during bone correction surgeries.

BACKGROUND OF THE INVENTION

One common type of bone deformity on a person's foot is a bunion. A bunion is a disease of the joint and soft tissue on a person's toes. Painful bunions are corrected through bone resection and realignment of the metatarsal bone, which are then fixed with a bone plate. Bone plates can irritate the patient's soft tissue and cause additional pain after bunion surgery. Therefore, a need exists for a bone fixation device which overcomes the above-noted problems.

SUMMARY OF THE INVENTION

Aspects of the present invention provide a medical implant used during bone correction surgeries, such as, an implant for securing portions of a patient's toe bone, for example, a metatarsal bone.

In one aspect, provided herein is an implant, including a plate portion at a first end and a stem portion at a second end extending away from an end of the plate portion.

In another aspect, provided herein is a surgical method, including preparing a patient's bones and performing an osteotomy on the patient's bones to form a first bone segment and a second bone segment. The method also includes aligning the first bone segment and the second bone segment and inserting an implant into an intramedullary canal of the second bone segment. The method further includes drilling at least one hole into the first bone segment through an opening in the implant and inserting at least one bone fastener through the opening in the implant and into the hole in the first bone segment. In addition, the method includes removing a bony overhang of the second bone segment to expose a plate center opening and drilling a third hole in the second bone segment through the plate center opening. Finally, the method includes inserting a bone fastener into the second bone segment through the plate center opening and completing the surgical procedure by closing an incision in the patient.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
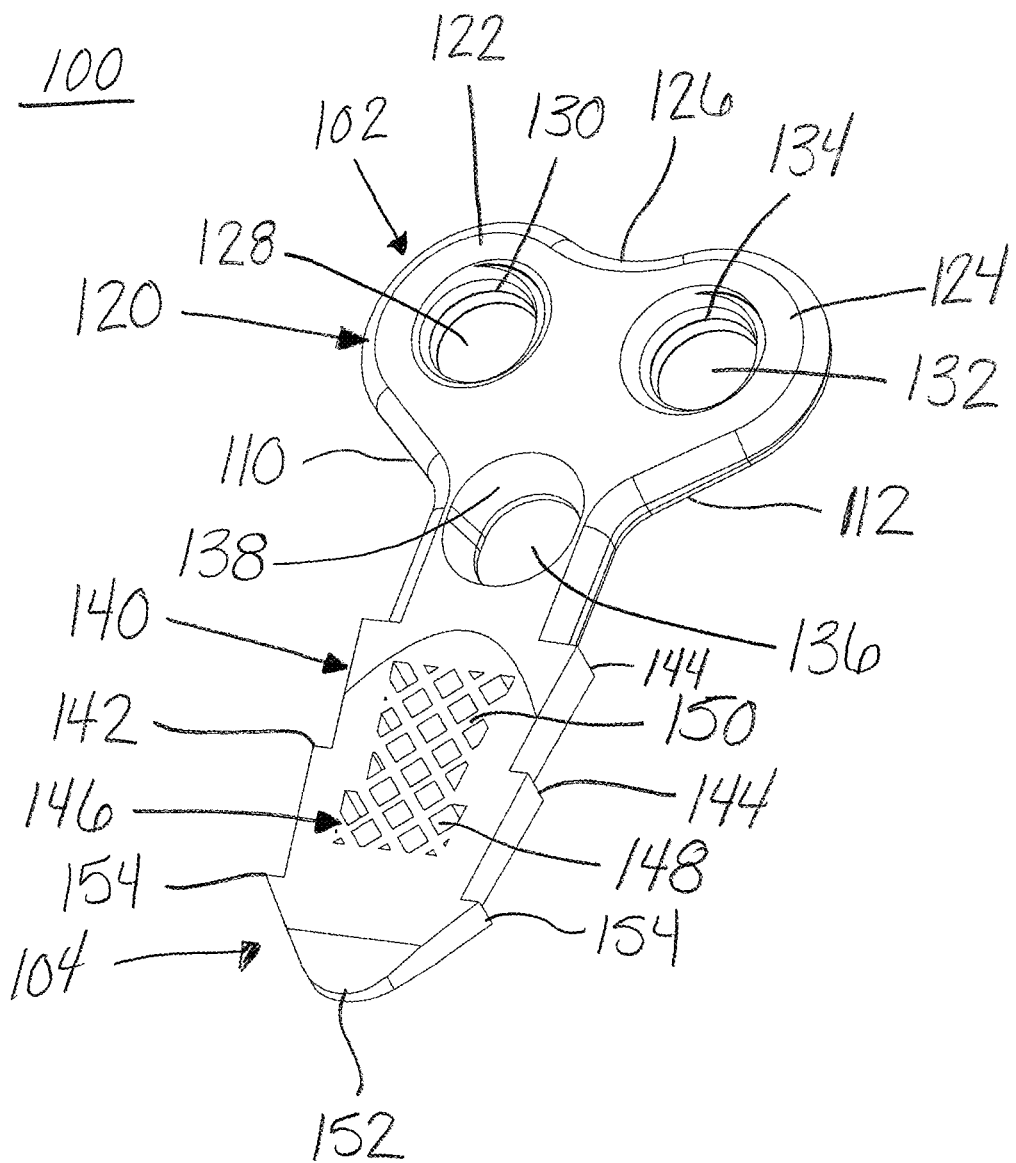
FIG. 1 is a perspective view of an implant, in accordance with an aspect of the present invention.

Generally stated, disclosed herein is an embodiment of a bone fixation device. The terms "bone fixation device," "bone fixation implant," "bunion correction device," "bunion device," "bunion correction implant," "bunion implant," "device," and "implant" may be used interchangeably as they essentially describe the same type of device. Further, a surgical methods for using the bone fixation device are discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. In addition, for the purposes of this disclosure when referencing the device, the term "proximal" will mean the portion of the device closest or nearest the insertion instrument. The term "distal" shall mean the portion of the device farthest away from the insertion instrument.

Referring to the drawings, wherein like reference numerals are used to indicate like or analogous components throughout the several views, and with particular reference to FIGS. 1-7, there is illustrated a bone fixation implant 100. The implant 100 may have a first end 102 opposite a second end 104, a top surface 106 opposite a bottom surface 108, and a first side 110 opposite a second side 112. The implant 100 including, for example, a plate or body portion 120 and a stem, insertion, or engagement portion 140. The plate portion 120 being positioned at the first end 102 and the stem portion 140 extending away from the plate portion 120 to the second end 104 of the implant 100, as shown in FIGS. 1-4 and 7.

In one embodiment, the top surface 106 of the implant may be, for example, polished to prevent soft tissue irritation, and the bottom surface 108 may include a surface roughness or texture to enable bone ongrowth, assists with resisting pull-out, and acts as a rasp when implanting and cutting bone. Although not explicitly shown, the implant 100 may further be curved in a medial-lateral direction to correspond to the natural shape of the patient's bone.

Figure 2:
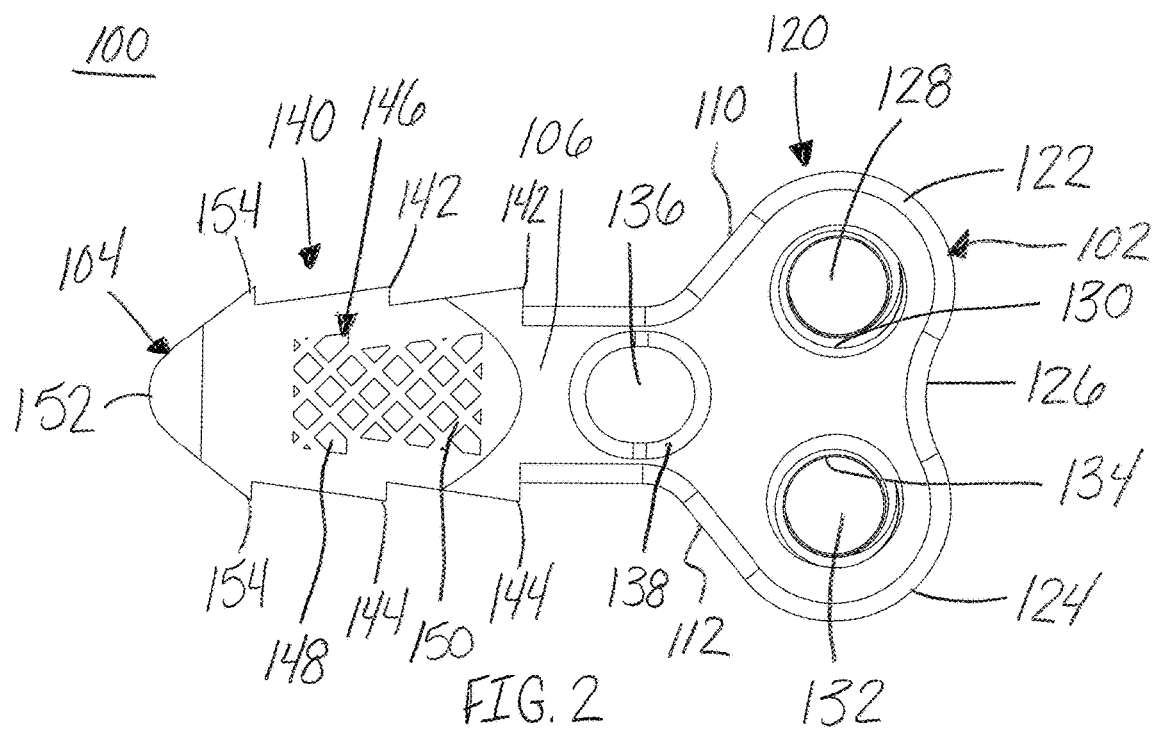
FIG. 2 is a top view of the implant of FIG. 1, in accordance with an aspect of the present invention.
Figure 3:
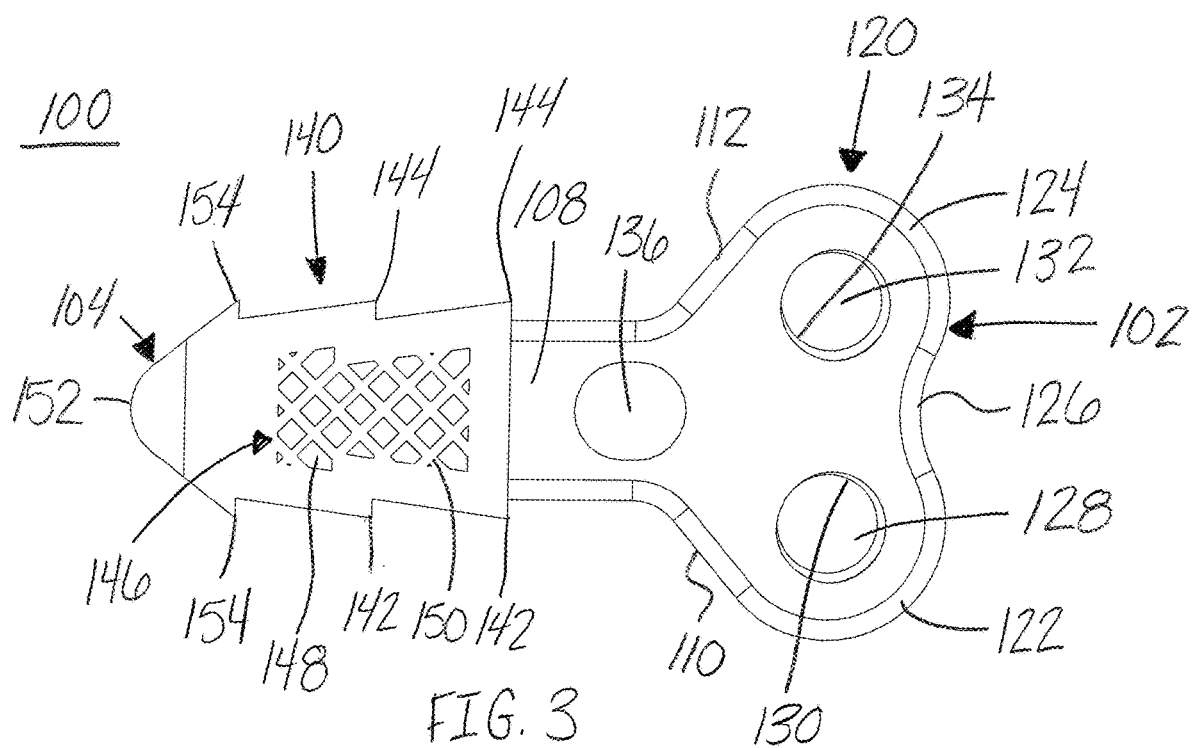
FIG. 3 is a bottom view of the implant of FIG. 1, in accordance with an aspect of the present invention.

With continued reference to FIGS. 1-7 and specifically FIGS. 1-3, the plate portion 120 may include a first lobe or ear 122 on the first side 110 of the implant 100 and a second lobe or ear 124 on the second side 112 of the implant 100. The first lobe 122 may include a first opening or screw hole 128. The first opening 128 may include threads 130 for coupling to the head of a bone fastener (not shown) with corresponding threads. The second lobe 124 may include a second opening or screw hole 132. The second opening 132 may include threads 134 for coupling to the head of a bone fastener (not shown) with corresponding threads. The plate portion 120 may also include a depression or inset region 126 positioned between the first and second lobes 122, 124 on the first end 102 of the implant 100. The threads 130, 134 of the first and second openings 128, 132 provide for a locking engagement between the plate portion 120 of the implant and any inserted locking fasteners to provide for bony fixation. However, it is also contemplated that the first and second openings 128, 132 may for some embodiments be non-threaded to allow for multi-axial placement of a bone fastener.

The stem portion 140 may include a central screw hole or opening 136 positioned adjacent to the plate portion 120, as shown in FIGS. 1-3 and 7. The opening 136 may include a surface 138 which may be, for example, angled or conical to receive the head of a bone fastener. The angled or conical surface 138 of the opening 136 allows for variable screw angulation insertion. The variable screw angulation insertion of opening 136 may be, for example, 30° in either direction to assist with compression and stabilization of the bone segments being joined.

The stem portion 140 may also include at least one first barb 142 positioned on the first side 110 of the implant 100 and at least one second barb 144 positioned on the second side 112 of the implant 100. The stem portion 140 may include, for example, two first barbs 142 and two second barbs 144, as shown in the depicted embodiment. As described in greater detail below, the stem portion 140 may also include insertion tip barbs 154 extending out from the first and second sides 110, 112 of the insertion tip 152. The stem portion 140 may include, for example, at least one barb, more specifically, between approximately three and ten barbs. The barbs 142, 144, 154 may be configured for a bone clearing broaching effect during insertion and to prevent pullout of the implant 100 after insertion into the patient's bone. The barbs 142, 144, 154 may be, for example, angled away from the longitudinal axis of the stem portion 140. The barbs 142, 144, 154, as shown in FIGS. 1-3, are symmetrical relative to each other, however it is contemplated that the barbs 142, 144, 154 on the first side 110 of the implant 100 may be offset from the barbs 142, 144, 154 on the second side 112 of the implant 100.

With continued reference to FIGS. 1-3 and 7, the stem portion 140 may also include a porous region, architecture or lattice 146 along at least a portion of the stem portion 140 which may be positioned centrally. The porous region 146 may include a plurality of openings 148 which extend through the stem portion 140 from the top surface 106 to the bottom surface 108 and a plurality of struts 148 to create the lattice structure 146. As explained further below, the stem portion 140 may be configured to be positioned within an intramedullary canal at a fusion site, such as at an osteotomy site (e.g., a fracture site), with the plate portion 120 positioned exterior to the site and in abutment with a side of a bone segment. The porous architecture of the stem portion 140 may thereby promote osteosynthesis (e.g., bone formation and ingrowth) on either side of the stem portion 140.

The porous region 146 of the stem portion 140 may be any architecture that provides openings or spaces at least in the engagement or exterior surfaces of the stem portion 140 that contact the bone. The openings or spaces of the stem portion 140 extend through the stem portion 140 such that bone is able to grow and penetrate into and within the stem portion 140. In some embodiments, the stem portion 140 may include a porosity, in the horizontal and/or vertical direction (e.g., along the proximal-distal and/or medial-lateral and/or plantar-dorsal directions) within the range of about 60% to about 90%, or within the range of about 65% to about 85%, or within the range of about 70% to about 80%. The porous region 146 of the stem portion 140 may be a defined or uniform architecture or pattern, may be a randomly generated or distributed architecture or lattice, or may include a different architecture in differing portions of the stem portion 140. As shown in FIGS. 1-3, the stem portion 140 may include a portion which includes the porous region 146. Also shown in FIGS. 1-3, the stem portion 140 may include a substantially uniform pattern of unit cells (e.g., substantially cubic or quadrilateral lattice structure). In some embodiments, the porous region 146 of the stem portion 140 may be formed of a structure of about 1 mm unit cells. In some embodiments, the porous region 146 of the stem portion 140 may be formed of interconnected elongate strut members 150. For example, in some embodiments the porous region 146 of the stem portion 140 may be formed, for example, of diamond cut interconnected elongate strut members 150 with a diameter within the range of about 0.1 mm to about 0.5 mm, or within the range of about 0.2 mm to about 0.4 mm, or about 0.3 mm. The porous region 146 of the stem portion 140 may be formed via diamond cutting (or a similar process) the structure and/or diamond cutting (or a similar process) struts or other members that are utilized to form the architecture.

Figure 4:
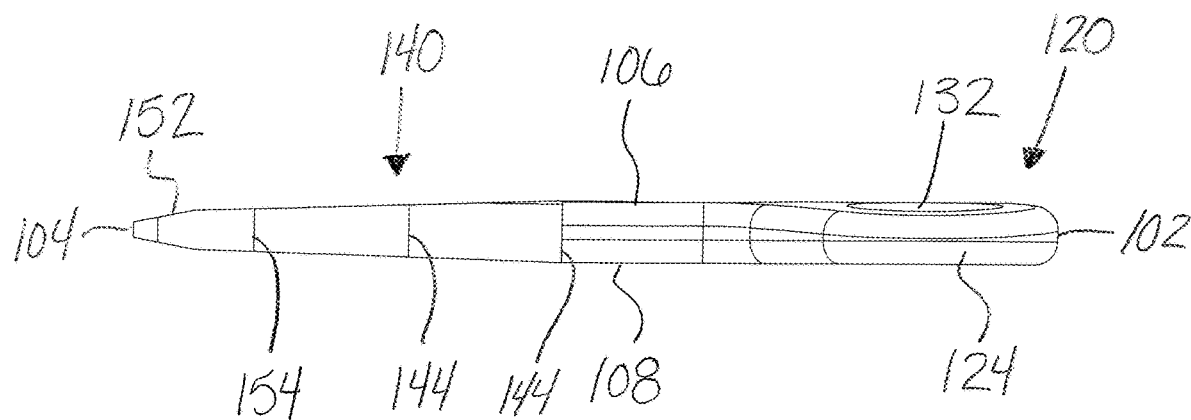
FIG. 4 is a side view of the implant of FIG. 1, in accordance with an aspect of the present invention.
Figure 5:
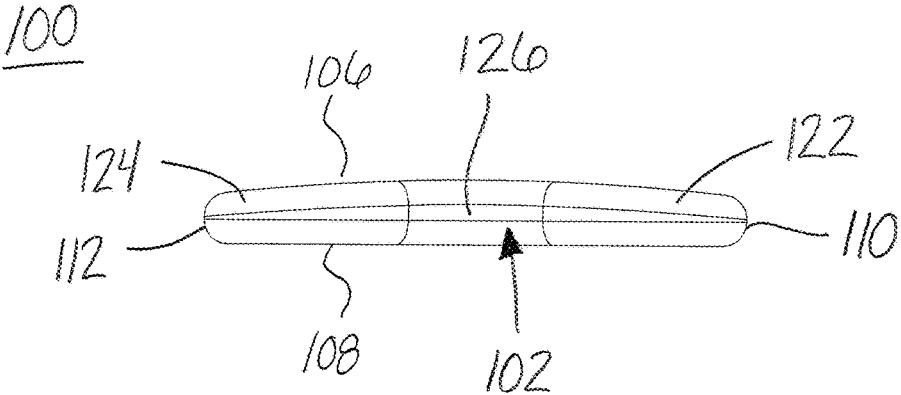
FIG. 5 is a first end view of the implant of FIG. 1, in accordance with an aspect of the present invention.
Figure 6:
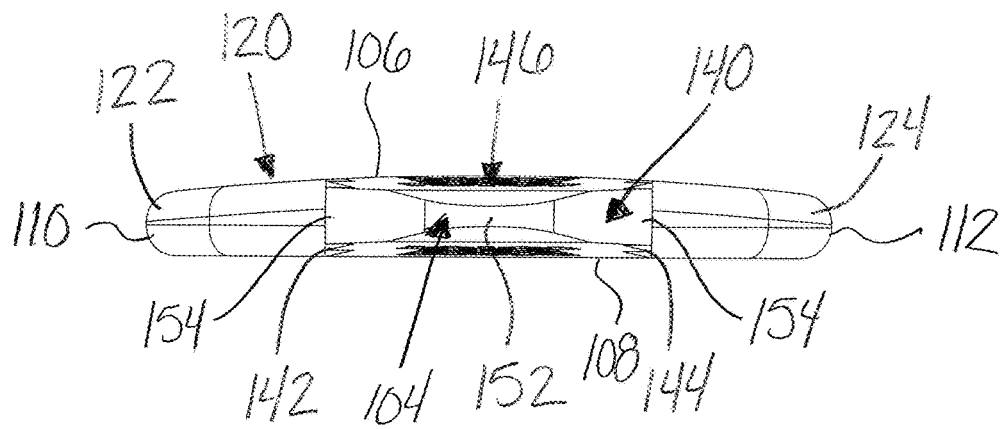
FIG. 6 is a second end view of the implant of FIG. 1, in accordance with an aspect of the present invention.
Figure 7:
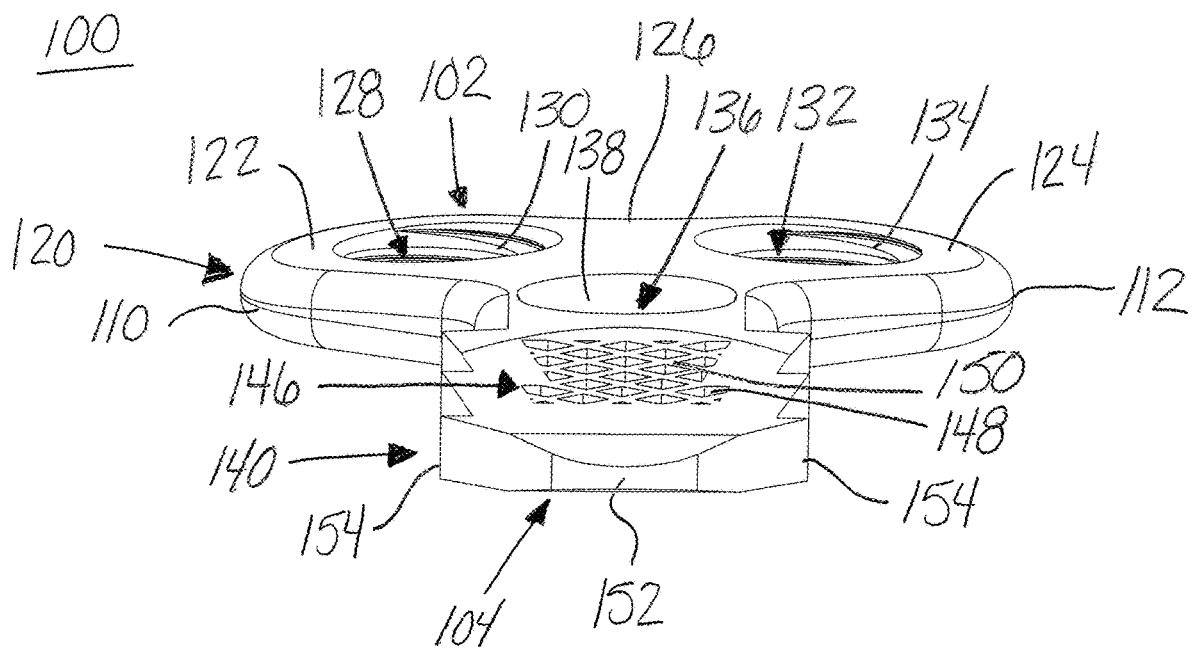
FIG. 7 is a perspective end view of the implant of FIG. 1, in accordance with an aspect of the present invention.

The stem portion 140 may further include an insertion end or tip 152, as shown in FIGS. 1-3 and 7. The insertion tip 152 may extend from the stem portion 140 to a generally pointed end at the second end 104 of the implant 100. The insertion tip 152 may include insertion tip barbs 154 extending out from the first and second sides 110, 112 of the insertion tip 152. The insertion tip barbs 152 may assist with bone clearing during insertion and securing the implant 100 in the patient's bone. The entire insertion tip 152 may be, for example, polished and tapered to provide for an easier insertion into the patient's bone segment, as best seen in FIGS. 4 and 7.

In one embodiment, the implant 100 may have, for example, a length of 30 mm and a thickness of 2 mm with barbs 142, 144 at approximately a 45° angle and having a length of approximately 5 mm. The implant 100 may further include, for example, a porous region 146 with diamond cut interconnected elongate strut members 150 with a diameter of 0.3 mm and a 1 mm unit cell with a porosity of approximately 70-79%. The implant 100 may be, for example, made of a medical grade titanium. The implant 100 may also be formed, for example, using additive manufacturing methods. The implant 100 may also include, for example, a stem portion 140 with a surface roughness and geometry for osteosynthesis in an intramedullary canal.

Figure 8:
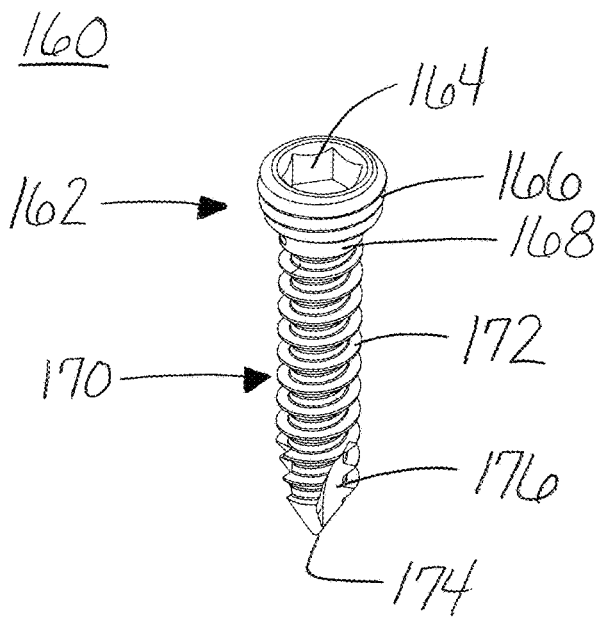
FIG. 8 is a top perspective view of a first bone fastener, in accordance with an aspect of the present invention.
Figure 9:
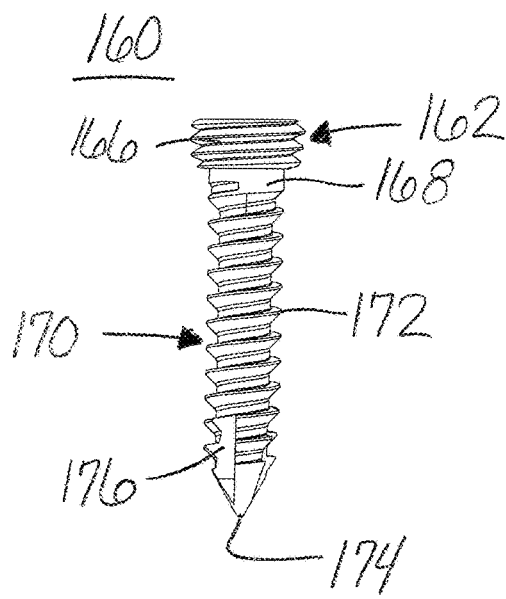
FIG. 9 is a side view of the first bone fastener of FIG. 8, in accordance with an aspect of the present invention.
Figure 10:
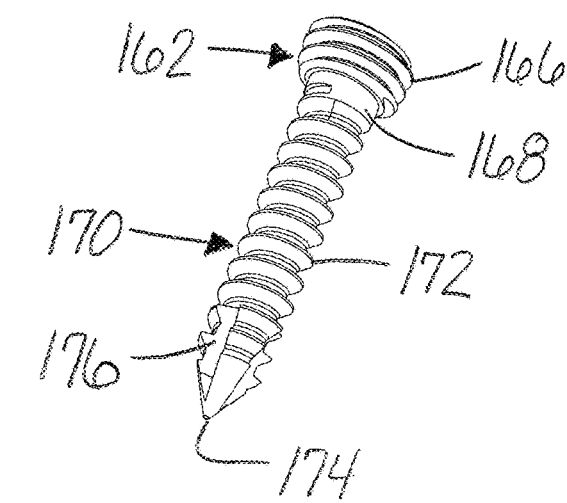
FIG. 10 is a bottom perspective view of the first bone fastener of FIG. 8, in accordance with an aspect of the present invention.

Referring now to FIGS. 8-10, there is illustrated a first bone fastener or screw 160. The first fastener 160 may include a head portion 162 coupled to a shaft portion 170 by a neck 168. The head portion 162 of the first fastener 160 may include an opening 164 for receiving a driver or drill to rotate the first fastener 160 for insertion or removal from a patient's bone. The opening 164 may have, for example, a polygonal shape, such as, a hexagonal shape. The head portion 162 of the first fastener 160 may also include threads 166 on the exterior surface of the head portion 162. In alternative embodiments, the head portion 162 may not include threads 166 and rather may have a smooth exterior surface. The neck 168 may be a relatively smooth region positioned between the threads 166 of the head portion 162 and the threads 172 of the shaft portion 170. The shaft portion 170 may include threads 172 extending along the length of the shaft portion 170 to a tip 174 of the first fastener 160. The tip 174 may include at least one cutting edge 176 to assist with insertion into a patient's bone.

Figure 11:
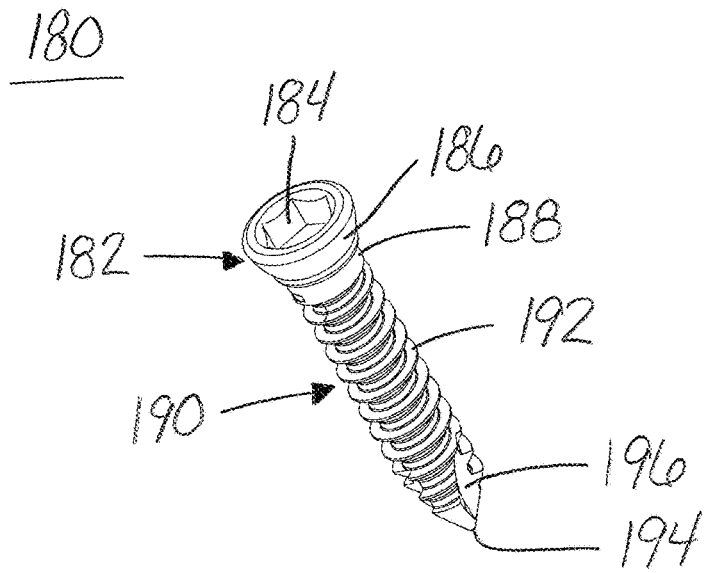
FIG. 11 is a top perspective view of a second bone fastener, in accordance with an aspect of the present invention.
Figure 12:
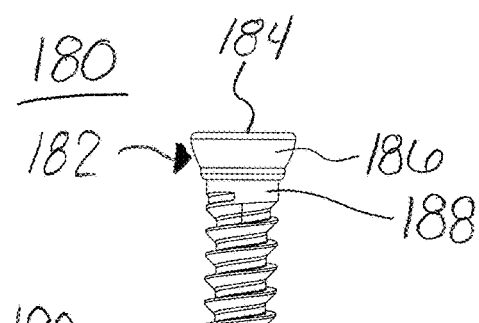
FIG. 12 is a side view of the second bone fastener of FIG. 11, in accordance with an aspect of the present invention.
Figure 13:
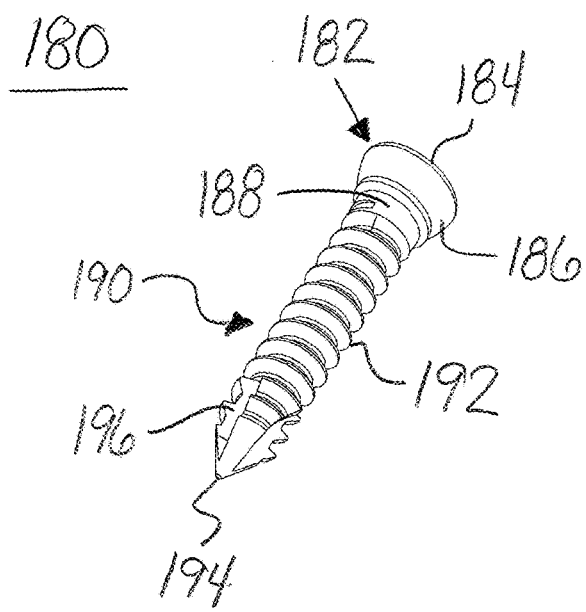
FIG. 13 is a bottom perspective view of the second bone fastener of FIG. 11, in accordance with an aspect of the present invention.

Referring now to FIGS. 11-13, there is illustrated a second bone fastener or screw 180. The second fastener 180 may include a head portion 182 coupled to a shaft portion 190 by a neck 188. The head portion 182 of the second fastener 180 may include an opening 184 for receiving a driver or drill to rotate the second fastener 180 for insertion or removal from a patient's bone. The opening 184 may have, for example a polygonal shape, such as, a hexagonal shape. The head portion 182 of the second fastener 180 may also include a tapered or curved exterior surface 186 extending from a top surface of the second fastener 180 to the neck 188 of the second fastener 180. The exterior surface 186 may have a shape, for example, that is curved to mate with the conical surface 138 of the central opening 136. The neck 188 may be a relatively smooth region positioned between the exterior surface 186 of the head portion 182 and the threads 192 of the shaft portion 190. The shaft portion 190 of the may include threads 192 extending along the length of the shaft portion 190 to a tip 194 of the second fastener 180. The tip 194 may include at least one cutting edge 196 to assist with insertion into a patient's bone.

Figure 25:
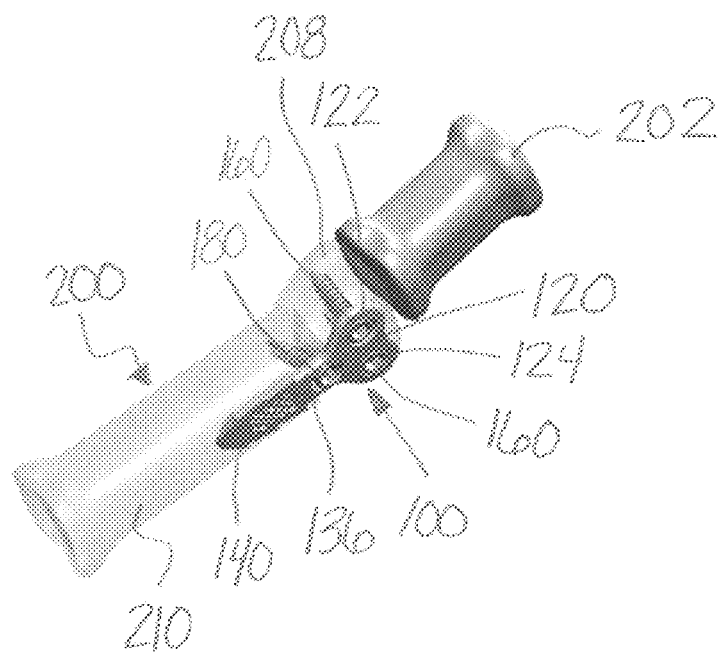
FIG. 25 is a perspective view of the bones and implant of FIG. 24 with a transparent bone showing the insertion position of the implant and bone fasteners, in accordance with an aspect of the present invention.
Figure 26:
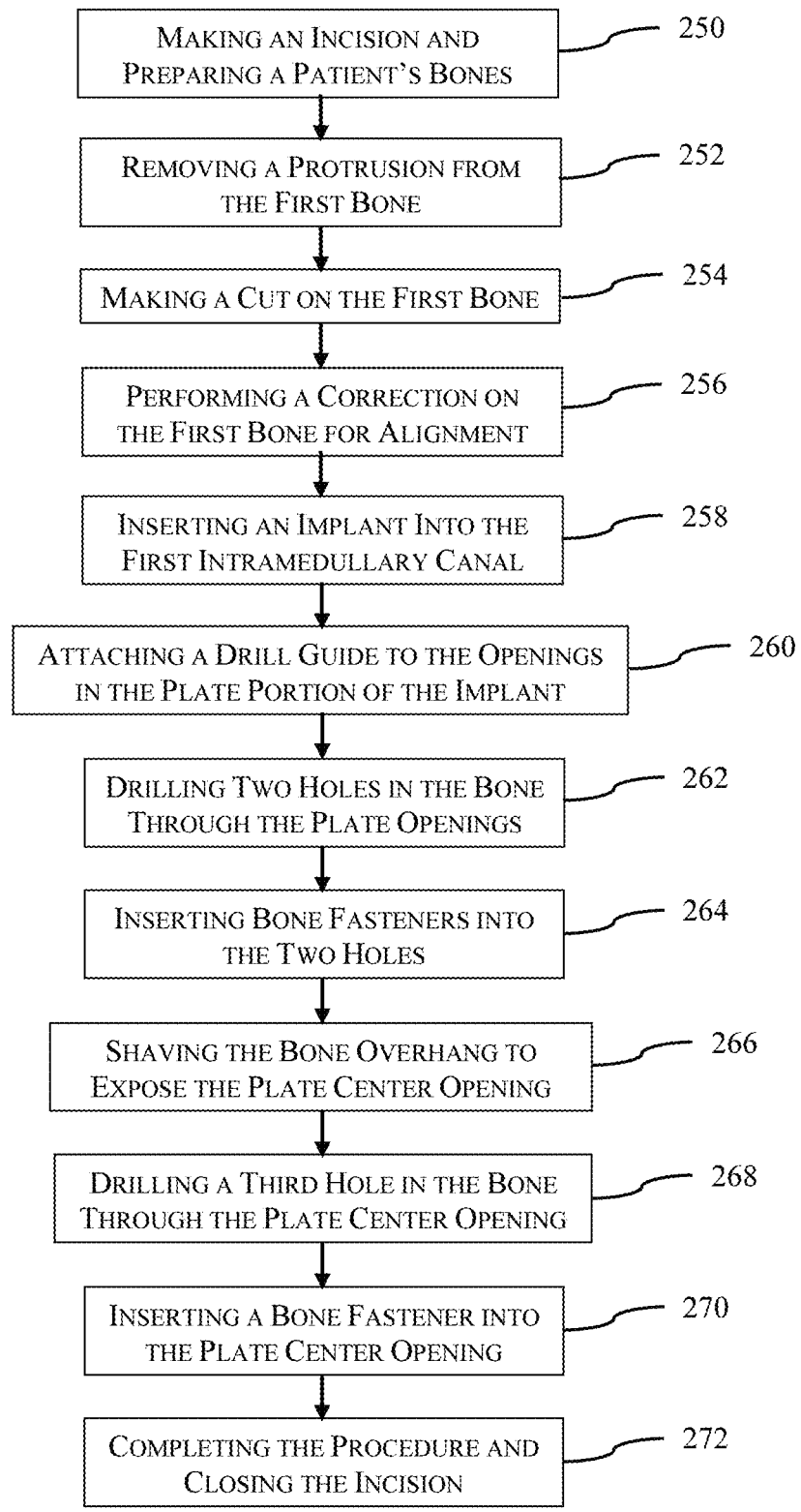
FIG. 26 depicts the surgical method of using the implant of FIGS. 1-7, in accordance with an aspect of the present invention.

Referring now to FIGS. 14-26, specifically to FIG. 26, a method of insertion of the implant 100 may include, for example, making an incision and preparing a patient's bones 250. The method may also include removing a protrusion from the first bone 252 and making a cut on the first bone 254. In addition, the method may include performing a correction on the first bone for alignment 256 and inserting an implant into the first intramedullary canal 258. The method may further include attaching a drill guide to the openings in the plate portion of the implant 260 and drilling two holes in the bone through the plate openings 262. The method may also include inserting bone fasteners into the two holes 264 and removing the bone overhang to expose the plate center opening 266. The method may still further include drilling a third hole in the bone through the plate center opening 268 and inserting a bone fastener into the plate center opening 270. Finally, the method may include completing the surgical procedure and closing the incision in the patient 272.

Figure 14:
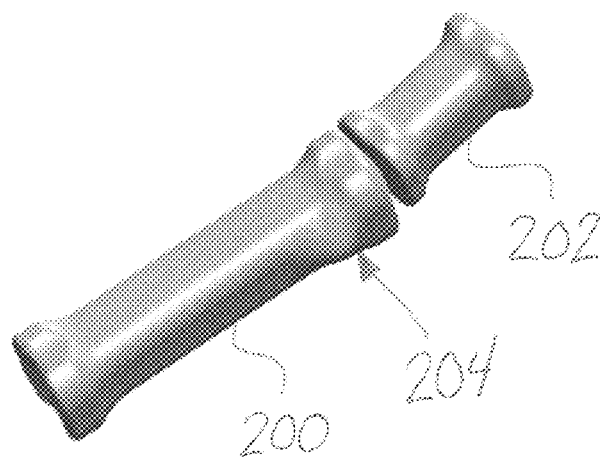
FIG. 14 is a perspective view of two bones with a bunion on one of the two bones, in accordance with an aspect of the present invention.
Figure 15:
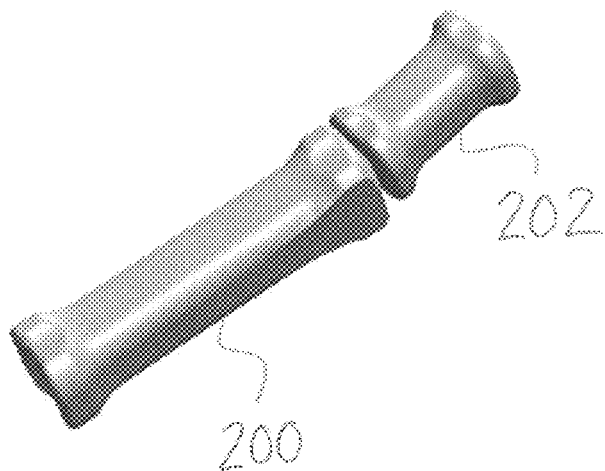
FIG. 15 is a perspective view of the bones of FIG. 14 after removal of the bunion, in accordance with an aspect of the present invention.
Figure 16:
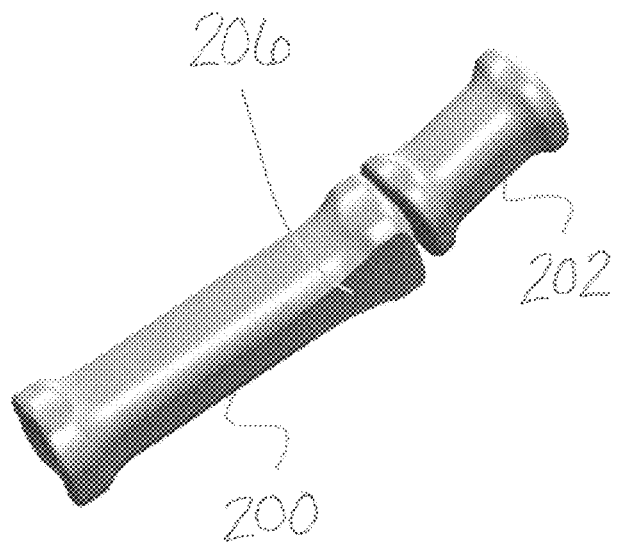
FIG. 16 is a perspective view of the bones of FIG. 15 after a Chevron osteotomy cut is performed, in accordance with an aspect of the present invention.
Figure 17:
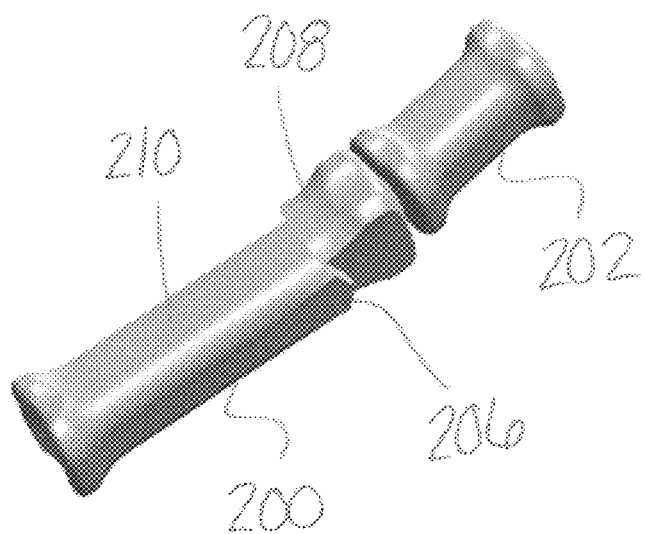
FIG. 17 is a perspective view of the bones of FIG. 16 after surgical correction has been performed, in accordance with an aspect of the present invention.

With continued reference to FIG. 26 and reference to FIGS. 14-25, the surgical method is shown in greater detail. Referring now to FIG. 14, a first bone 200 with a medial protrusion or bump 204 and a second bone 202 are shown. In one embodiment, the first bone 200 may be, for example, a first metatarsal, the medial protrusion 204 may be, for example, a bunion, and the second bone 202 may be, for example, a proximal phalanges. The bunion 204 may then be removed, as shown in FIG. 15. Next, an osteotomy may be performed, for example, a Chevron osteotomy, to perform a cut 206 in the first bone 200, as illustrated in FIG. 16. The cut 206 may form a first segment 208 and a second segment 210 of the first bone 200. Referring now to FIG. 17, the first and second segments 208, 210 may then be re-aligned to surgically correct the bone deformity.

Figure 18:
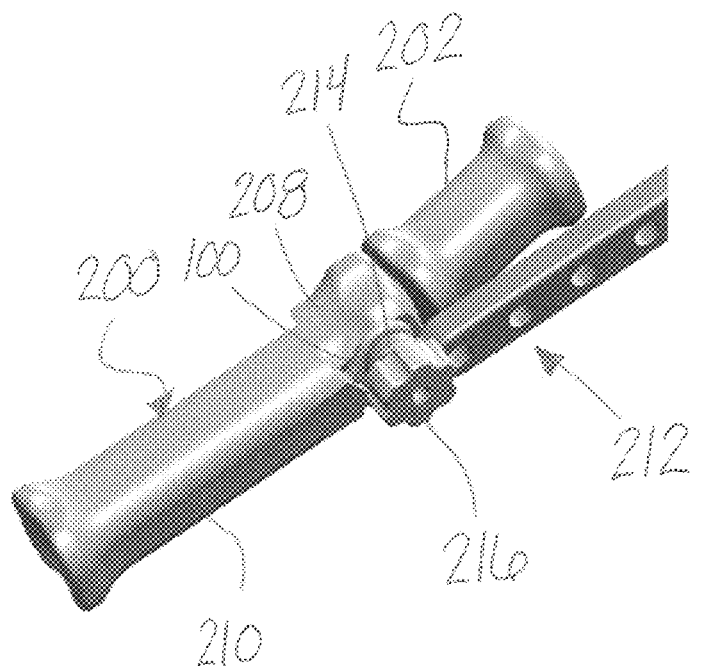
FIG. 18 is a perspective view of the bones of FIG. 17 after insertion of the implant of FIGS. 1-7 into the intramedullary canal of the cut bone and a drill guide coupled to the implant, in accordance with an aspect of the present invention.
Figure 19:
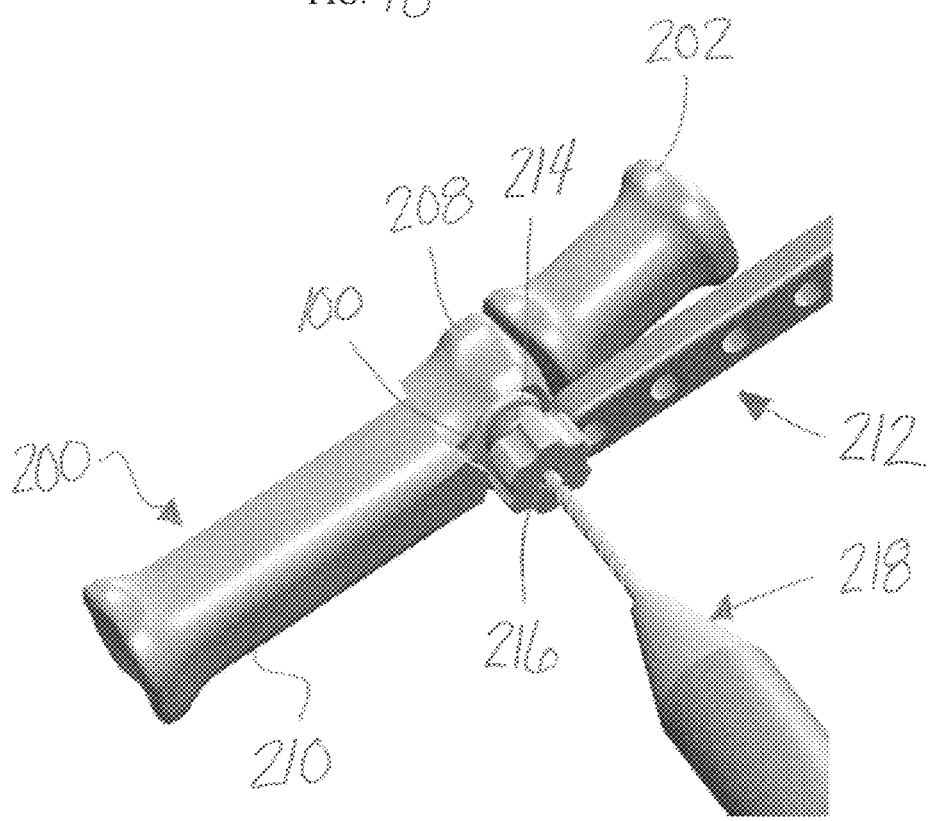
FIG. 19 is a perspective view of the bones with the inserted implant and coupled drill guide of FIG. 18 as a drill is inserted into a bone through the drill guide and implant, in accordance with an aspect of the present invention.
Figure 20:
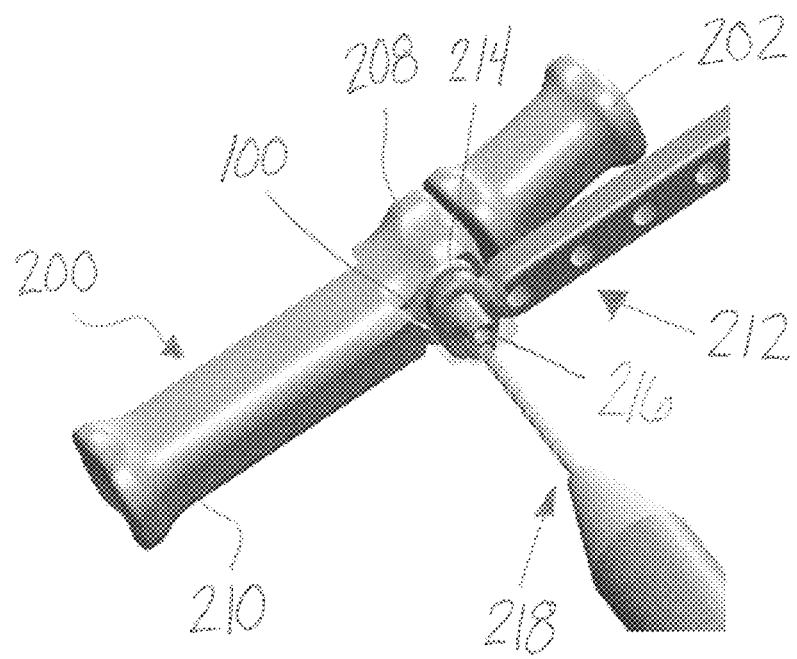
FIG. 20 is a perspective view of the bones, implant and coupled drill guide of FIG. 19 after drilling two openings into the bone through the implant and drill guide, in accordance with an aspect of the present invention.
Figure 21:
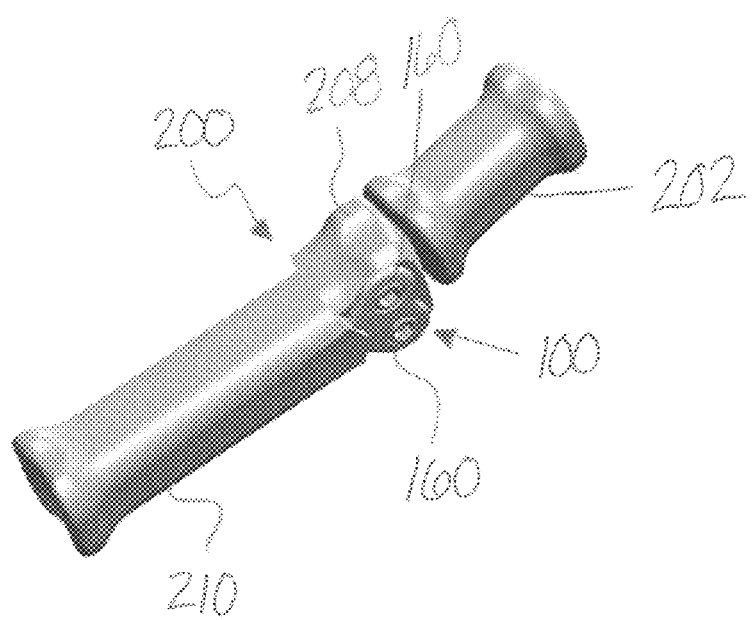
FIG. 21 is a perspective view of the bones and implant of FIG. 20 with two bone fasteners inserted into the bone through the implant, in accordance with an aspect of the present invention.

Once the bone segments 208, 210 are aligned, the stem portion 140 of the implant 100 may be inserted into the intramedullary canal of the second segment 210 of the first bone 200, as illustrated in FIG. 18. Then an engagement end 214 of a drill guide 212 may be coupled to the openings 128, 132 of the implant 100. The drill guide 212 may include at least one drill opening 216 for receiving a drill 218 for drilling holes into the first segment 208 of the first bone 200 through the openings 128, 132 in the implant 100, as shown in FIGS. 19 and 20. Next, as shown in FIG. 21, bone fasteners 160 may be inserted through the openings 128, 132 in the implant 100 and into the second segment 208 of the first bone 200. The head portions 162 of the first fasteners 160 having threads 166 which correspond to the threads 130, 134 in the openings 128, 132 of the plate portion 120 of the implant 100 to secure the first fasteners 160 to the implant 100.

Figure 22:
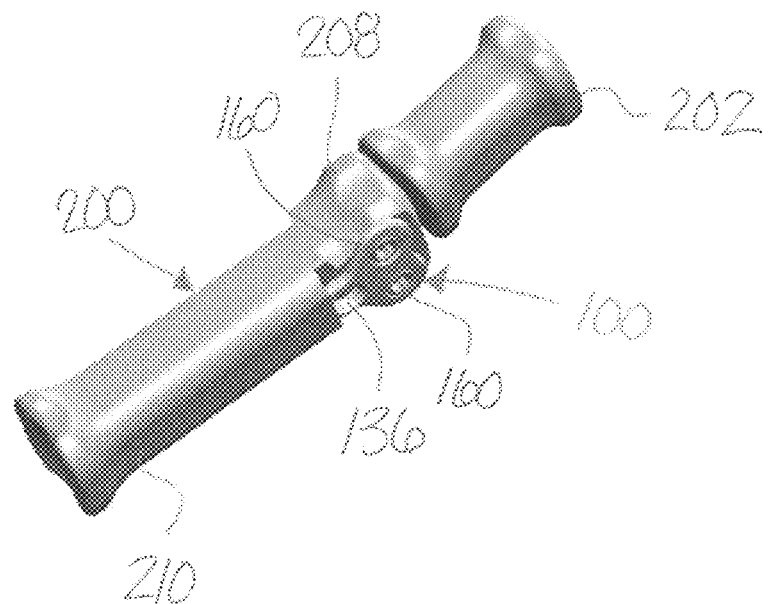
FIG. 22 is a perspective view of the bones and implant of FIG. 21 after removing the portion of the bone overhang to expose the central opening, in accordance with an aspect of the present invention.
Figure 23:
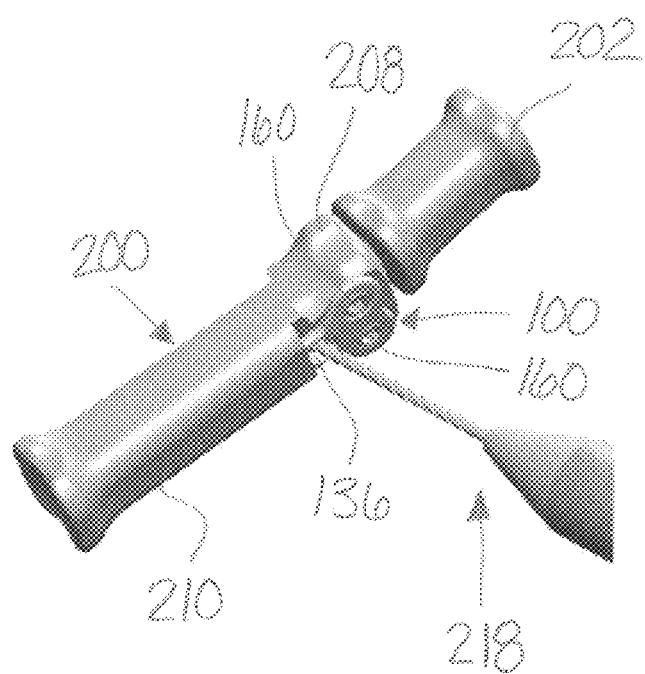
FIG. 23 is a perspective view of the bones and implant of FIG. 22 after drilling a hole through the central opening into the bone, in accordance with an aspect of the present invention.
Figure 24:
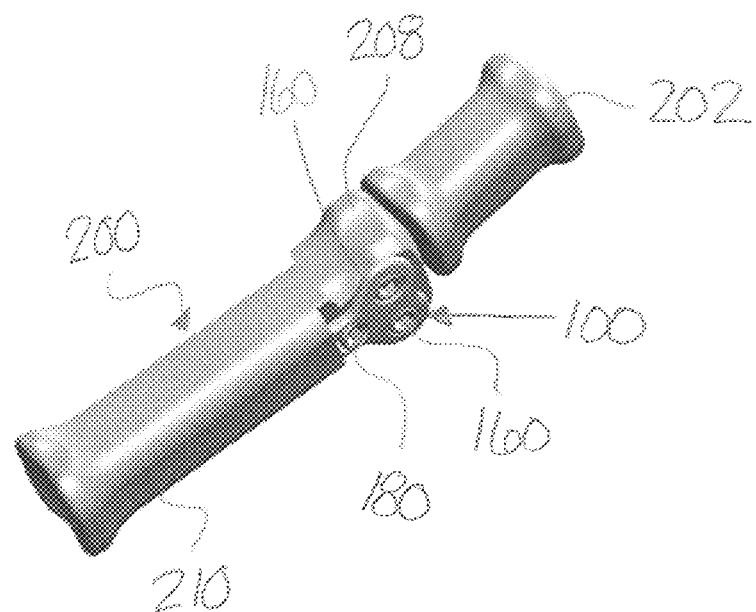
FIG. 24 is a perspective view of the bones and implant of FIG. 23 after inserting a third bone fastener into the bone through the central opening, in accordance with an aspect of the present invention.

After the plate portion 120 of the implant 100 is secured to the first segment 208 of the first bone 200, the overhanging portion of the second segment 210 of the first bone 200 may be removed to expose the central opening 136, as shown in FIG. 22. Once the central opening 136 is exposed, a drill 218 may be used to drill an opening into the second segment 210 of the first bone 200, as shown in FIG. 23. Although not shown, a drill guide may be used to drill the hole in the bone segment 210 through the central opening 136. Next, as shown in FIGS. 24 and 25, a bone fastener 180 may be inserted through the central opening 136 of the implant 100 and into the second segment 210 of the first bone 200. The tapered or curved exterior surface 186 of the second fastener 180 mates with the angled or curved edge 138 of the central opening 136 to enable the second fastener 180 to be inserted at various angles to allow for the desired compression and stabilization. Finally, the procedure may be completed and the patient's incision closed.

Figure 27:
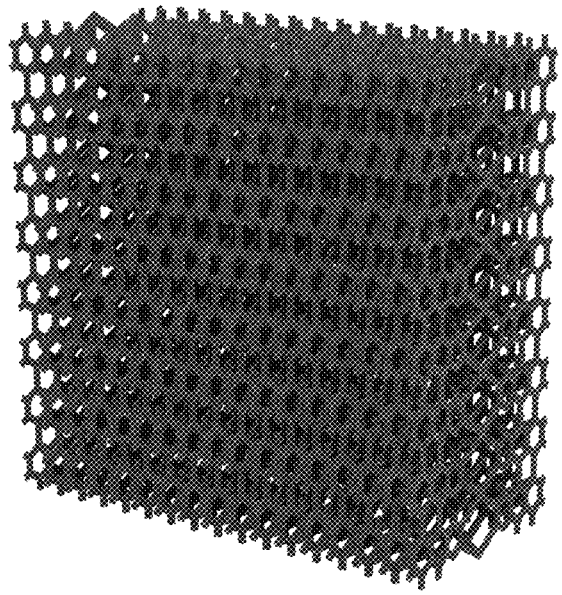
FIG. 27 is a perspective view of a porous region.
Figure 28:
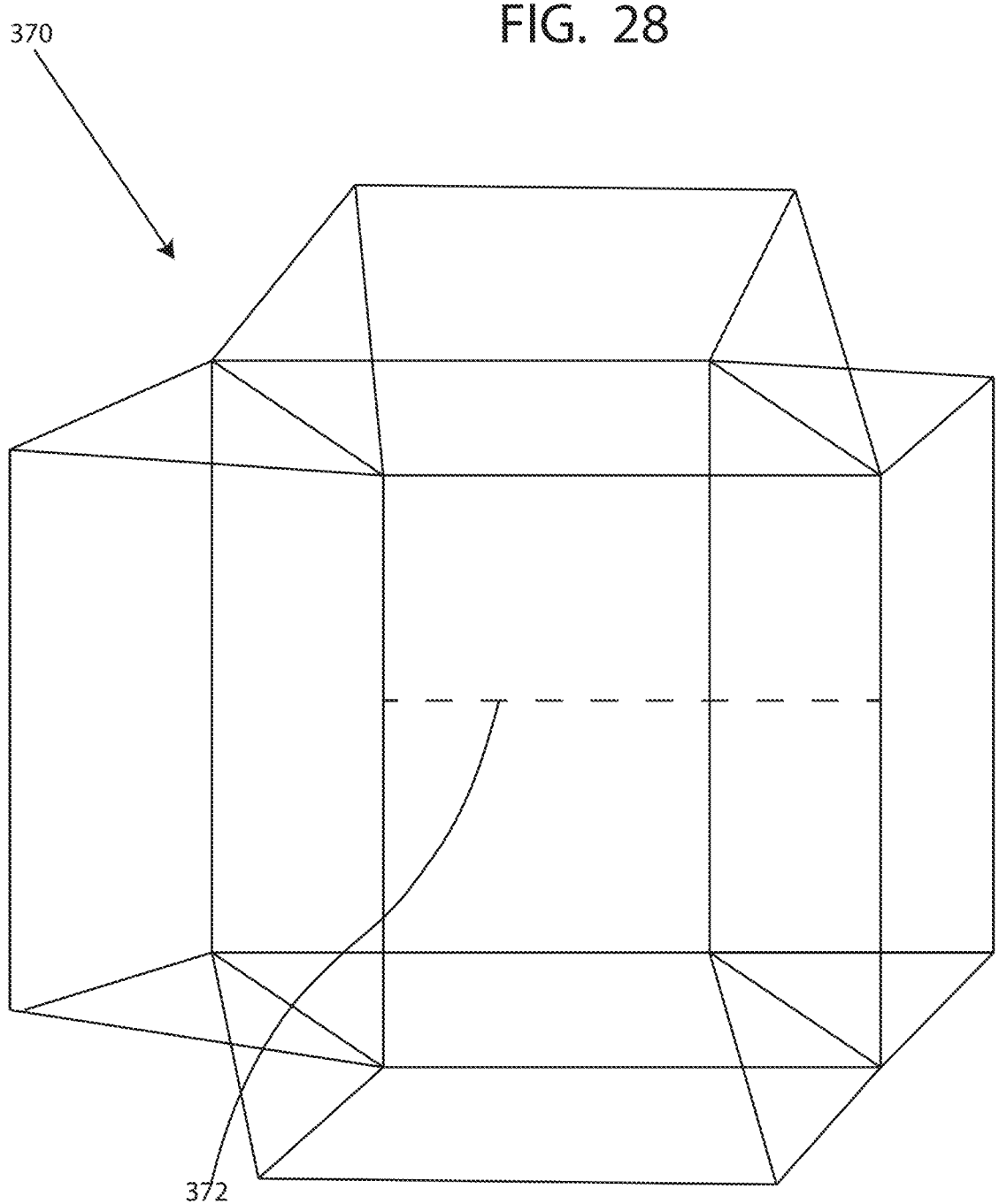
FIG. 28 is a front view of a honeycomb structure of a porous region.

FIG. 27 is a perspective view of a porous region 340 that can be used in the porous region 146. This porous region 146 or 340 can have a standard lattice structure that can be either variable in porosity across a cross-sectional profile or have a standard porosity profile. Each of the cells or units of the porous region 146 or 340 can have any suitable or desirable shape which can include but is not limited to a pentagon, a hexagon, a square, a quadrangle and a honeycomb pattern. An example of this pattern is shown in FIG. 28 which shows a honeycomb pattern 370, which is a pattern for each cell of a porous region or any suitable cell of a porous region. The honeycomb pattern has a width or opening such as width or opening 372. As the porosity and thereby the density of the structure changes, the width or size of this opening 372 can change as well. For example, in a less porous structure, or more dense structure, the distance across 372 could be less. However, in a less dense structure or more porous structure, the distance across 372 could be more.

Figure 29A:
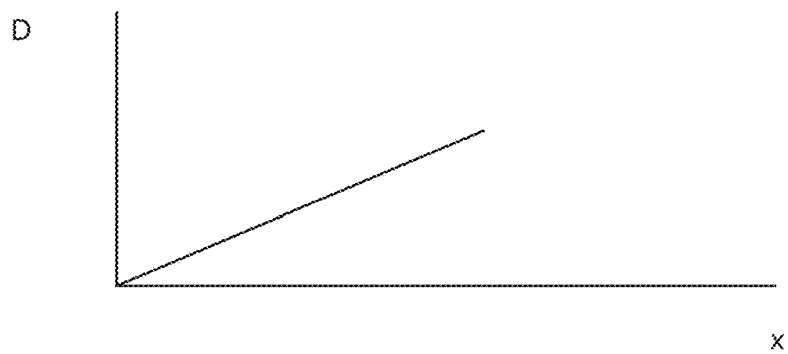
FIG. 29A is a density profile across a cross-section of the porous region.
Figure 29B:
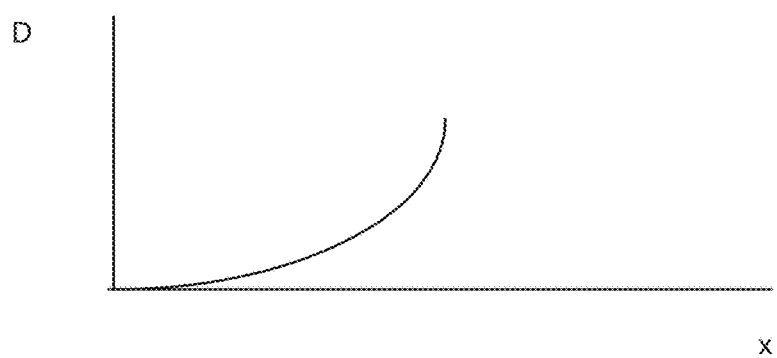
FIG. 29B is a density profile across a cross section of the porous region from the outside of the porous region to an interior region.
Figure 29C:
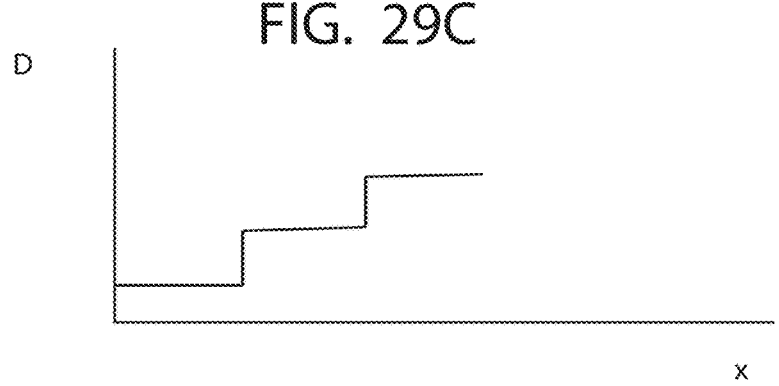
FIG. 29C is a density profile across a cross-section of the porous region from the outside of the porous region to an interior region.
Figure 29D:
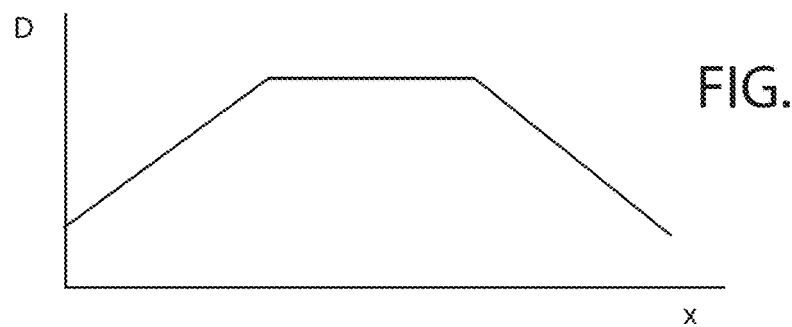
FIG. 29D is a density profile across a cross-section of the porous region from the outside of the porous region to an interior region.
Figure 30A:
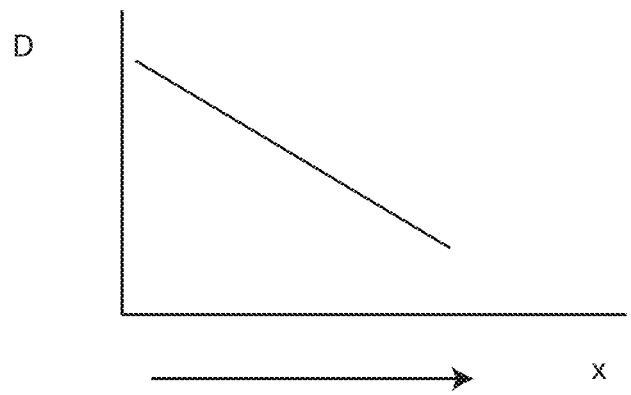
FIG. 30A is a density profile across a cross-section of the porous region from the outside of the porous region to an interior region.
Figure 30B:
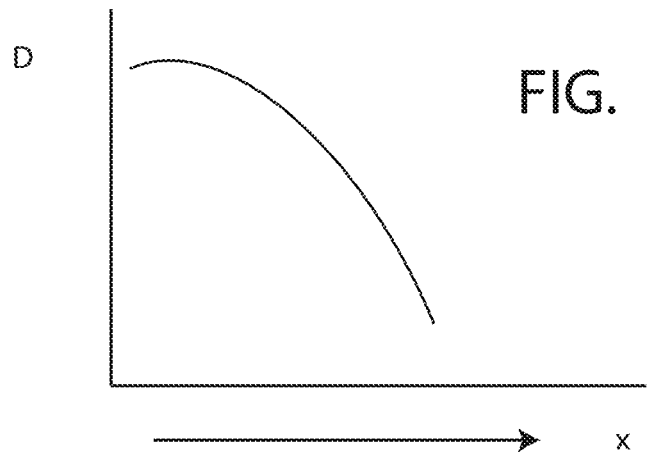
FIG. 30B is a density profile across a cross-section of the porous region from the outside of the porous region to an interior region.
Figure 30C:
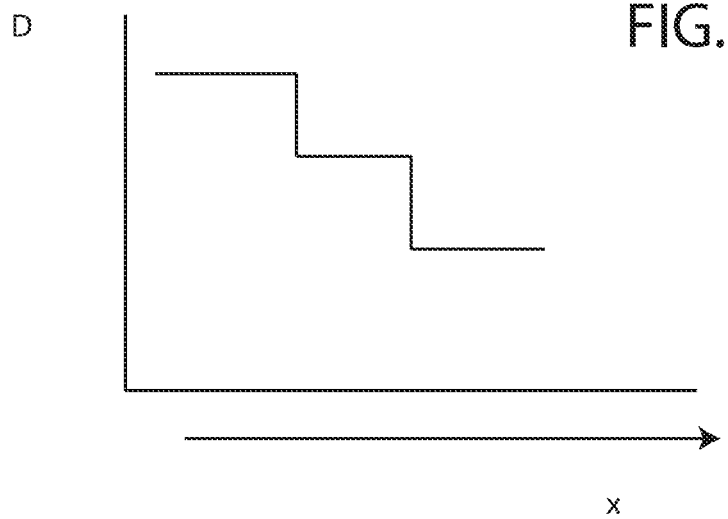
FIG. 30C is a density profile across a cross-section of the porous region from the outside of the porous region to an interior region.

The porosity or density of the porous region 146, 340 such as that of each cell can vary across a cross-sectional profile. For example, FIG. 29A shows a steadily increasing density of the structure from an outside region towards an inner region of the porous structure 146 and 340. FIG. 29B shows an alternative porosity profile which shows an ever increasing density from an outside region towards an inner region of the porous region 146. FIG. 29C shows a stepwise increase in density across a cross-sectional profile from outside towards inside, while FIG. 29D shows an increasing and then decreasing density of the porous region 146, 340. Conversely FIG. 30A shows a steadily decreasing density from an outer region of the porous region 146, 340. FIG. 30B shows an increasing or accelerating decrease in density across the cross section of the porous region 146, 340. FIG. 30C shows a step wise decrease in density from an outer region towards an inner region of the porous region 146 and 340. While these porosity profiles can be variable on one side they can also be variable from both sides of the porous regions 146, 340, therefore from both sides of the porous region, the porosity and thereby the density can be variable.

Figure 31A:
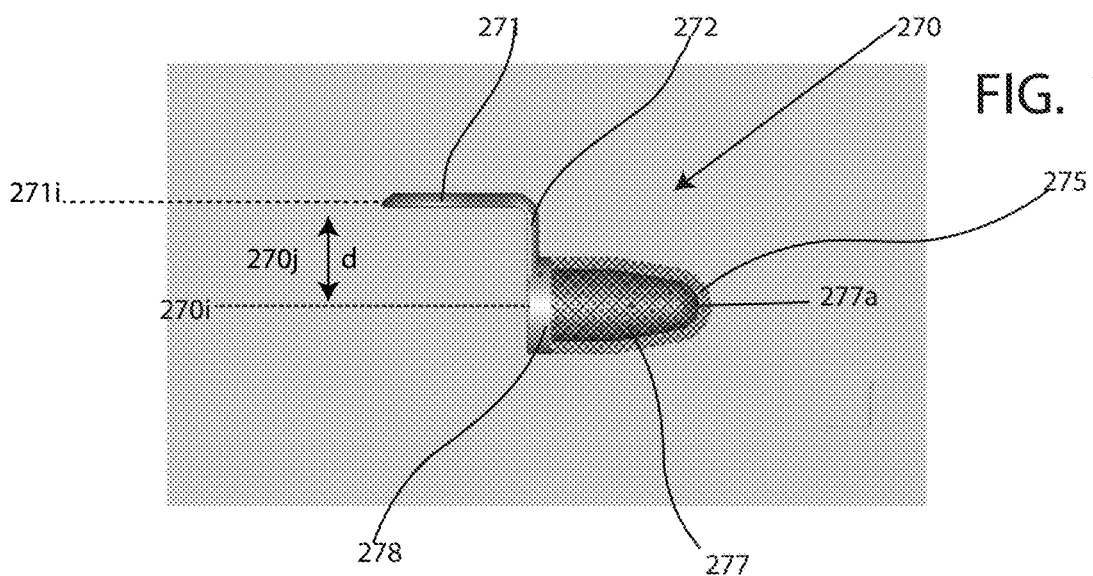
FIG. 31A is a side view of another embodiment.
Figure 31B:
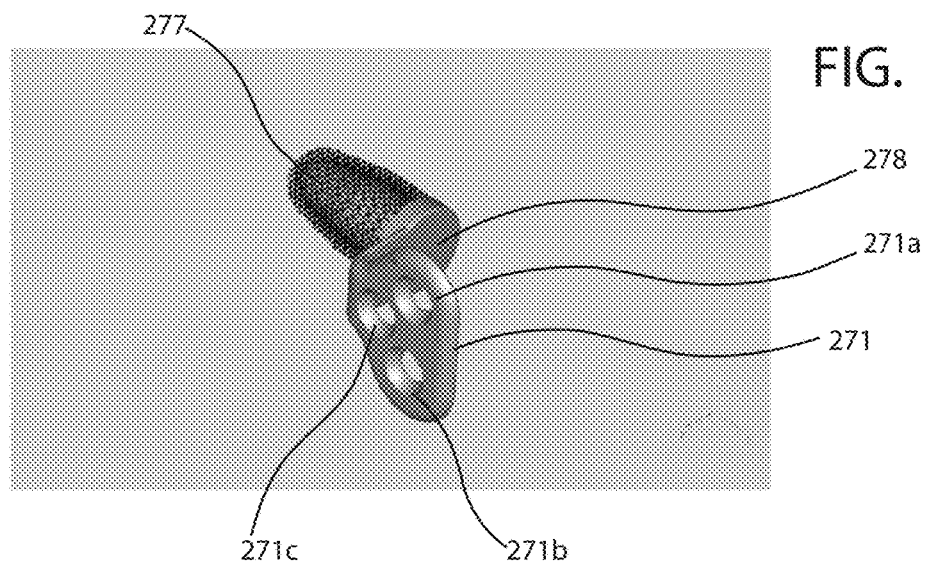
FIG. 31B is an end perspective view of the embodiment of FIG. 31A.
Figure 31C:
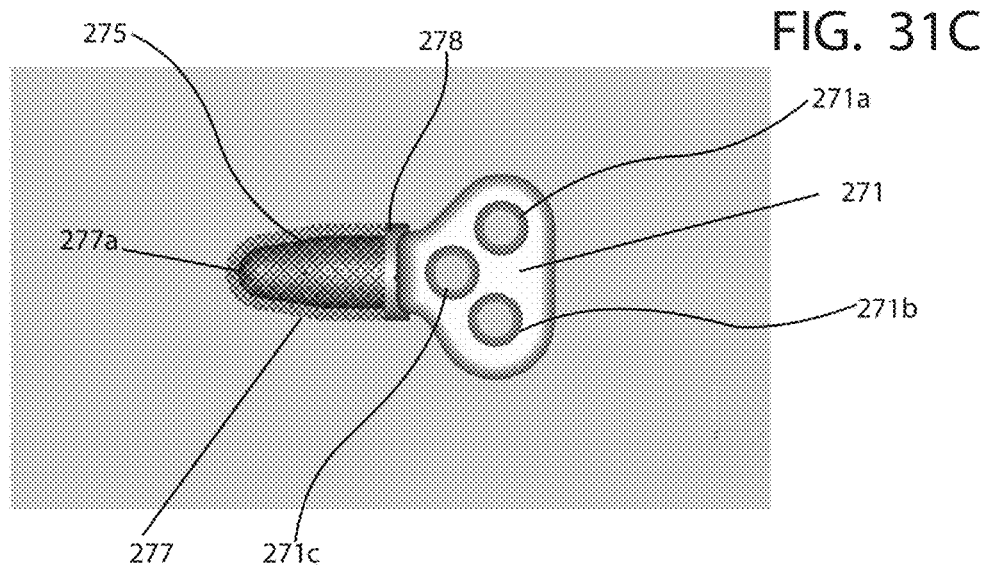
FIG. 31C is a top or plan view of the embodiment of FIG. 31A.

FIG. 31A is a side view of another embodiment FIG. 31B is an end perspective view of the embodiment of FIG. 31A; and FIG. 31C is a top or plan view of the embodiment of FIG. 31A. With these views, the plug 270 comprises a plate section 271, a joining section 272, which is coupled to the plate section at a first end and coupled to a stopper 278 at a second end. Plate section 271 and joining section 272 combine to form a substantially L-shaped plate. There is also a plug body 277, and a cage 275 formed by a mesh screen. Plate section 271 includes screw holes for receiving orthopedic screws to fix plate section 270 to an adjacent bone. In addition, plug body 277 is configured to be shaped in a bulbous manner having an elongated body that has an increasingly narrower section which ends at a rounded end 277a. Plug 270 is configured to be inserted into an open end of a bone such as a cleanly fractured bone. Plate 271 is then configured to be clamped or screwed into an adjacent bone. In addition, FIG. 31A shows two axis lines 270i and 270j. Axis line 270i is the longitudinal axis for a center region of the plug body 277, axis line 271i is the longitudinal axis for the plate and corresponds to a bottom surface of the plate. Arrow 270j denotes the distance d from the axis line 270i to the axis line 271i. This distance d can be varied depending on the need in the form of an offset based upon bone structure. For example, in at least one embodiment, this distance d could vary from any number from 1-20 mm. Alternatively, the distance d is bridged by the length of joining section 272 as well as a portion of the radius of stopper 278.

Figure 32:
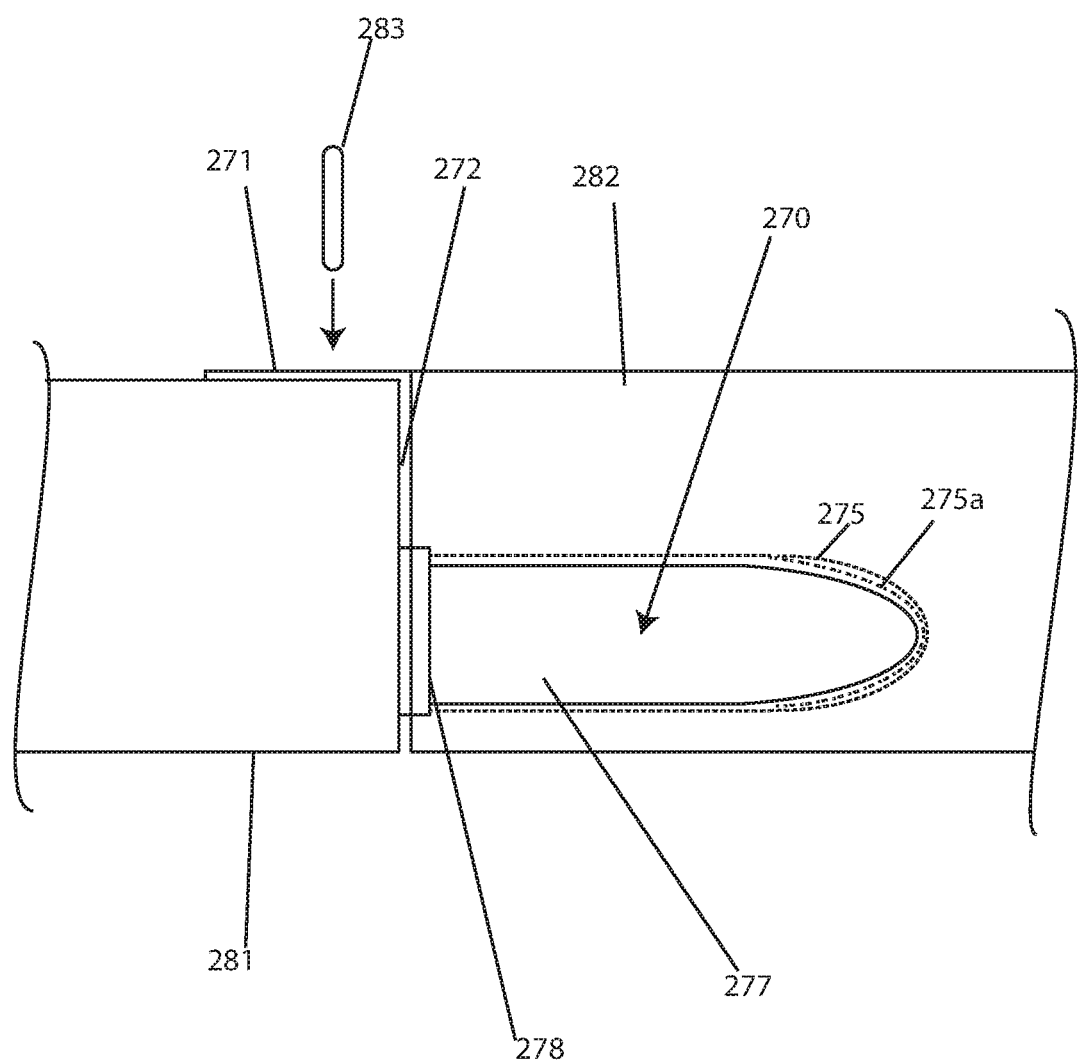
FIG. 32 shows a side view of a plug coupled to two portions of a bone.

FIG. 32 shows an open side view of a plug inserted into a bone and configured to fuse to adjacent broken bones together. Plug body 277 as well as the lattice mesh structure or cage 275 is configured in at least one embodiment to fit inside a canal of a bone. For example, there are two adjacent pieces of bone 281, and 282. These two bones can be fused together via the insertion of plug 270 wherein plug body 277 which is a solid bulbous body inserts into an end of bone 282 and plate 271 is clamped to a top or side portion of bone 281 via fasteners such as fastener 283. The fasteners are configured to fit through holes 271a, 271b, and 271c. Each of these holes have a beveled interface to receive a screw head flush to the surface of the plate 271. The cage or mesh section 275 is configured to intermesh with bone 282 such that it forms multiple interfaces to promote bone growth. In at least one embodiment, the mesh or cage section can have a variable lattice structure of different shapes or porosity such as that disclosed in FIGS. 27-30C. For example, the lattice mesh structure can have a greater porosity on the outer regions of the cage and less porosity as the cage approaches body 277 such as between line 275a and plug 270. Alternatively, the lattice mesh structure 275 can have a lower porosity (thereby greater density) on the outer regions of the cage and a higher porosity and less density as the lattice or mesh structure approaches the body 277. Thus, the lattice mesh structure can be of lower density between line 275a and the solid plug 270, vs. the lattice mesh structure between line 275a and the outer region of the lattice mesh. Furthermore, the lattice can have multiple different shapes such as a diamond shape or a honeycomb shape as well.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. A plug for coupling at least two bones together comprising:
    a plug body wherein said plug body is a solid bulbous body and substantially elongated and has a rounded end;
    a plate coupled to the plug body wherein the plate has a L-shape and wherein the plate has at least one hole;
    wherein the plug body is configured to be coupled to a first bone, and said plate is configured to be coupled to a second bone and wherein the plug is configured to couple at least two bones together; and
    a mesh cage coupled to the plug body wherein the mesh cage has porosity.

2. The plug as in claim 1, wherein the mesh cage has a variable porosity.

3. The plug as in claim 2, wherein the mesh cage has a lattice structure which has a plurality of cells that are either honeycomb shaped or diamond shaped.

4. The plug of claim 1, wherein the plate comprises:
    a first lobe with a first screw hole; and
    a second lobe with a second screw hole, wherein the first lobe is adjacent to the second lobe.

5. The plug of claim 1, wherein the mesh cage has a variable porosity such that the exterior of the porous region has a lower porosity than the interior region.

6. The plug of claim 1, wherein the mesh cage has a variable porosity such that the exterior of the porous region has a higher porosity than the interior region.

7. The plug of claim 1, further comprising at least one fixation element configured to couple said implant to an adjacent bone.

8. The plug of claim 7, wherein said at least one fixation element is a screw.

9. The plug as in claim 8, wherein said screw has a cutting edge.

10. The plug of claim 1, wherein said bulbous body is shaped as an elongated body that has an increasingly narrower section and which ends at a rounded end.

11. The plug as in claim 1, further comprising at least one stopper, wherein said stopper is coupled to said plate, said plug body and said mesh cage.

12. The plug as in claim 11, wherein said stopper is substantially cylindrical in shape and which has a diameter that extends beyond said plug body to connect to said mesh cage.

13. The plug as in claim 12, wherein said L-shaped plate is coupled to said stopper and has at least a joining section coupled to said stopper and a plate section extending transverse to said joining section.

* * * * *

UNITED STATES PATENT AND TRADEMARK OFFICE
CERTIFICATE OF CORRECTION

| | | |
|---|---|---|
| PATENT NO. | : 11,058,468 B2 | Page 1 of 1 |
| APPLICATION NO. | : 15/665097 | |
| DATED | : July 13, 2021 | |
| INVENTOR(S) | : Parekh et al. | |

It is certified that error appears in the above-identified patent and that said Letters Patent is hereby corrected as shown below:

On the Title Page

In the Assignee (73): Delete "ADDITIVE ORTHOPAEDICS, LLC" and insert -- PARAGON ADVANCED TECHNOLOGIES, INC. --

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*